(12) United States Patent
Pedersen

(10) Patent No.: US 6,284,501 B1
(45) Date of Patent: Sep. 4, 2001

(54) INTERESTERIFICATION OF PHOSPHOLIPIDS

(75) Inventor: Kim Brint Pedersen, Koebenhavn (DK)

(73) Assignee: Novozymes A/S, Bagsvaerd ( * ) Notice: Subject to any disclaimer, the term of this patent is extended or adjusted under 35 U.S.C. 154(b) by 0 days.

(21) Appl. No.: 07/828,856

(22) PCT Filed: Aug. 29, 1990

(86) PCT No.: PCT/DK90/00222

§ 371 Date: Feb. 3, 1992

§ 102(e) Date: Feb. 3, 1992

(87) PCT Pub. No.: WO91/05056

PCT Pub. Date: Apr. 18, 1991

(30) Foreign Application Priority Data

Oct. 4, 1989 (DK) .................................... 4872/89

(51) Int. Cl.[7] ................ C12P 9/00; C12P 13/00

(52) U.S. Cl. ............ 435/131; 435/128; 435/188; 435/196; 435/197; 435/212

(58) Field of Search .................. 435/131, 128, 435/212, 196, 197, 188

(56) References Cited

U.S. PATENT DOCUMENTS 4,382,035   5/1983   Eibl ............................ 260/403

OTHER PUBLICATIONS

Muratova et al., Biochem., vol. 52, No. 7, pp. 919–922 (1988).
Franck et al., Z. Naturforch, vol. 23 b, pp. 439–448 (1968).
Georke et al., Biochim. Biophys. Acta, vol. 248, pp. 245–253 (1971).

*Primary Examiner*—Herbert J. Lilling
(74) *Attorney, Agent, or Firm*—Elias J. Lambiris; Jason I. Garbell

(57) ABSTRACT

Specific exchange of the acyl group in the sn-2 position of a phospholipid is achieved by reacting it with a free fatty acid in the presence of an extracellular phospholipase $A_2$.

20 Claims, No Drawings

INTERESTERIFICATION OF PHOSPHOLIPIDS

TECHNICAL FIELD

This invention relates to a process for modifying a phospholipid by specific exchange of the acyl group in the sn-2 position.

BACKGROUND ART

For some applications of phospholipids it is desirable to specifically incorporate fatty acyl groups into the sn-2 position of the molecule, e.g. in order to modify the emulsification properties, to increase the stability against oxidation or to improve the physiological or nutritional value of the phospholipid.

It has been described that exchange of acyl groups in diacylphospholipids can be catalyzed by native or derivatized lipase (JP-A 63-185,391, JP-A 63-105,686). These lipases are known to possess activity against primary alcohols or primary esters, so during phospholipid interesterification a significant fraction of the incorporated fatty acids is incorporated into the sn-1 position of the phospholipids.

It is known from U. Z. Muratova et al., Biochemistry (USSR), 52(7), 919–922 (1988) that purified phospholipase $A_2$ from rat liver mitochondria membranes catalyzes ester exchange between phospholipid and fatty acid, but practical use of this finding has never been considered. The enzyme is very unstable, especially in purified form, it has a low specific activity as a hydrolytic enzyme, and does not appear amenable to economical production.

H. P. Franck et al., Z. Naturforsch. 23b, 439–448 (1968) reported that under appropriate conditions, snake venom phospholipase $A_2$ could be used to remove the acyl group from the sn-2 position of a phospholipid (to form lysophospholipid) and then to reinsert the fatty acid. However, J. Goerke et al., Biochim. Biophys. Acta, 248, 245–253 (1971) reported that this finding was due to misinterpretation of results.

Apart from these erroneous conclusions of H. P. Franck et al., commercially available phospolipases $A_2$ from snake or bee venoms or of pancreatic origin have never been described as being capable of interesterifying phopholipids although these enzymes are very well described with regard to hydrolytic properties, of which for instance their strict specificity towards the sn-2 position of phospholipids are well known.

It is the object of the invention to provide a process for modifying a phospholipid by specific exchange of the acyl group in the sn-2 position, using a readily available enzyme with high specific activity, such that a high degree of incorporation of a desired fatty acid can be obtained.

STATEMENT OF THE INVENTION

Very surprisingly, it has been found that it is possible to achieve the desired exchange reaction of phospholipid by reacting it with a free fatty acid in the presence of an extracellular phospholipase $A_2$. In contrast to mitochondrial phospholipase $A_2$ these enzymes are known to have high specific activity and to be extremely stable even at temperatures above 70° C.

Accordingly, the invention provides a process for modifying a phospholipid by specific exchange of the acyl group in the sn-2 position, characterized by reacting the phospholipid with a free fatty acid in the presence of an extracellular phospholipase $A_2$.

Phospholipid

The process of the invention may be applied to any desired kind of glycero-phospholipid containing a fatty acyl ester group in the sn-2 position, particularly to 1-alkyl-2-acyl-phospholipid (ether-phospholipid) and to diacyl-phospholipid.

Fatty acid

The exchange reaction of the invention may be used to incorporate any desired fatty acid into a phospholipid. Some examples of fatty acids that may be of particular interest are:

Long-chain ($C_{18}$–$C_{22}$) polyunsaturated fatty acid, such as linoleic, arachidonic, alpha-linolenic, eicosapentaenoic, docosahexaenoic or gammalinolenic acids. These may be incorporated to improve the physiological or nutritional value of the phospholipid, especially a diacyl-phospholipid.

$C_2$–$C_{18}$ saturated fatty acids. These may be incorporated to modify emulsification properties, to modify the physiological value or to improve oxidation stability of a phospholipid, especially a diacyl-phospholipid.

Acetic acid may be incorporated into an ether-phospholipid to prepare compounds with hormonal activity.

Phosgholipase $A_2$ preparation

The extracellular phospholipase $A_2$ to be used is preferably a venom enzyme (especially from bee venom or snake venom) or a digestive enzyme (especially from pancreas, e.g. porcine pancreas). To ensure the specific incorporation into the sn-2 position of a phospholipid the phospholipase $A_2$ preparation should be essentially free of phospholipase $A_1$, phospholipase B or lipase activity.

An example is Lecitase™ (product of Novo Nordisk a/s), a preparation of porcine pancreatic phospholipase $A_2$ containing virtually no lipase activity.

A suitable dosage of phospholipase for obtaining a high degree of exchange in a reasonable time is generally in the range 5,000 to 100,000 IU/g of phospholipid. The units of activity (IU), mentioned in this specification are measured as described in G. H. de Haas et al., Biochim. Biophys. Acta, 159, 103–117, (1968).

For the practice of the invention the phospholipase may be precipitated or immobilized on a suitable carrier, e.g. formed by precipitation on silica (celite) particles or by adsorption on a suitable carrier, e.g. an adsorbent resin of the acrylic type an example of which is Lewatit E 2001/85 (product of Bayer). The catalysts are typically loaded with 10,000–100,000 IU per g (dry weight) of catalyst.

Process conditions

The interesterifying process should be carried out under conditions at which both the phospholipid and the fatty acid are miscible in a fluid phase, e.g. solubilized in an organic solvent that also allows the enzyme catalyst to be active. The solvent may be hexane, heptane, petroleum ether or chlorinated hydrocarbons. Alternatively, the phospholipid may be solubilized directly in the fatty acid.

The process temperature should be chosen after considering thermostability of the phospholipase. Generally 20–80° C. will be suitable.

The process may be carried out as a batch reaction, where the ingredients are stirred gently throughout the reaction period. The amount of phospholipase preparation in the reaction mixture will typically be 1–10% w/w, and the reaction time will generally be ½–72 hours, preferably ½–24 hours.

Alternatively, the process may be carried out continuously by letting the substrate mixture (and solvent, if used) pass through a fixed bed column of phospholipase catalyst. The residence time will typically be 1–12 hours.

The amount of water in the reaction system should be controlled, since a certain water activity is required to activate the immobilized phospholipase, but too high water content may cause complete hydrolysis of the phospholipid into lysophospholipid. A suitable water content is generally 0.01–1% (w/w) of the total reaction system.

Furthermore the water should contain some $Ca^{++}$ e.g. provided as $CaCl_2$, as $Ca^{++}$ is an essential cofactor for venom and pancreatic phospholipases $A_2$. A suitable $Ca^{++}$ concentration in the water phase is 1 mM–1 M.

In a batch system the water containing $Ca^{++}$ may be provided by hydrating the phospholipase $A_2$ catalyst with a solution of $Ca^{++}$ before reaction, preferably to 0.5–15% water by weight. In a continuous column system, water containing $Ca^{++}$ may be introduced by hydrating the catalyst as above, and further by having some water dissolved in the substrate.

In processes where polyunsaturated fatty acids are to be incorporated into phoapholipids, it may be essential to protect the fatty acids from oxidation. This can be done by running the reaction under a blanket of an appropriate non-oxidizing gas like nitrogen, helium or argon.

After the reaction, the modified phospholipid may be recovered by conventional methods.

EXAMPLE

Two samples of phospholipase $A_2$ catalyst were prepared as follows:

Sample 1

150 ml of a solution containing $1.5 \times 10^6$ IU phospholipase $A_2$ (Lecitase), 10 mM $CaCl_2$ at a pH of 8 was added to 60 g of celite (Hydrosupercel A, product of Manville). 600 ml acetone at 0° C. was added. After 30 minutes at 0° C. phospholipase precipitated on celite was filtered off and flushed with 400 ml acetone at 0° C. The residual acetone were allowed to evaporate, and the preparation was then vacuum dried. The resulting preparation had a dry weight content of 99.6% (w/w) and a phospholipase load of 28,200 IU per g (dry weight) of catalyst.

Sample 2

180 ml of a sample containing $1.5 \times 10^6$ IU phospholipase $A_2$ (Lecitase), 10 mM $CaCl_2$ at a pH of 8 was added to 60 g (dry weight) of a macroporous acrylic-type adsorbent resin (Lewatit® 2001/85) and gently stirred at room temperature overnight. Phospholipase immobilized on adsorbent resin was filtered off and flushed with a solution of 10 mM $CaCl_2$ at a pH of 8 followed by vacuum drying. The resulting preparation had a dry weight content of 98.3% (w/w) and a phospholipase $A_2$ load of 27,900 IU per g (dry weight) of catalyst.

As phospholipid was used the commercial product Epikuron 200 from Lucas Meyer GmbH. This is a fractionated soybean lecithin claimed to contain min. 95% phosphatidyl choline, max. 4% lysophosphatidyl choline and a moisture and oil content of max. 3%. 5.5 g of Epikuron 200 was mixed with 15.9 g myristic acid and 90 ml petroleum ether (b.p. 80–100° C.). In this mixture the molar ratio of myristic acid to phosphatidyl choline is approx. 10:1. Each of the samples mentioned above corresponding to a dry weight of 125 mg were weighed into vials. The phospholipase preparations were humidified overnight at room temperature to a water content of 8% w/w using a solution of 100 mM $CaCl_2$ at pH 8.

1.5 ml of the above substrate were added to each phospholipase sample. Gentle stirring was then carried out at 40° C. for 24 hours.

After the reactions the composition of fatty acids in the phosphatidyl choline was assayed as follows: Phosphatidyl choline was separated from fatty acids and lysophosphatidylcholine by thin layer chromatography on Silica gel 60 plates (Merck art. 5721) using $CHCl_3$: $CH_3OH$: $H_2O$ (65:25:4, v/v/v) as solvent. After elution the plates were dried, and bands visualized by iodine vapors. The band corresponding to phosphatidyl choline was scraped off. Fatty acids in the phosphatidyl choline in the scrape-off were methylated and the fatty acyl methyl esters were determined and quantitated by gas chromatography.

The results were:

After the reactions most of the initially present phosphatidyl choline had become hydrolyzed, but still significant fractions of phosphatidyl choline remained.

Remaining phosphatidyl choline treated with phospholipase sample 1 and sample 2 contained myristic acid in amounts of 43% (w/w) and 40% (w/w), respectively, of the total amount of fatty acid. For comparison the phosphatidyl choline before reaction contained virtually no (less than 0.5% (w/w)) myristic acid.

What is claimed is:

1. A process for modifying a phospholipid by specific exchange of the acyl group in the sn-2 position, characterized by reacting the phospholipid with a free fatty acid in the presence of an extracellular phospholipase $A_2$.

2. A process according to claim 1 for modifying a 1-alkyl-2-acyl-phospholipid or a diacyl-phospholipid.

3. A process according to claim 1 or 2, wherein the extracellular phospholipase $A_2$ is a venom enzyme or a digestive enzyme, and is essentially devoid of phospholipase $A_1$, phospholipase B and lipase activity.

4. A process according to claim 1, wherein the amount of phospholipase in the reaction system corresponds to an activity of 5,000–100,000 IU/g of phospholipid.

5. A process according to claim 1, wherein the phospholipase $A_2$ is immobilized or precipitated on a suitable carrier.

6. A process according to claim 1, wherein the amount of water in the reaction system is 0.01–1% (w/w).

7. A process according to claim 1, wherein $Ca^{++}$ is present in the water phase.

8. A process according to claim 1, wherein the water content of the phospholipase catalyst prior to the reaction is 0.5–15% (w/w).

9. A process according to claim 1, wherein the temperature is 20–80° C.

10. A process according to claim 1, carried out in the presence of an organic solvent.

11. A continous process according to claim 1, wherein a mixture containing phospholipid, fatty acid and (optionally) solvent is passed through a fixed bed of phospholipase $A_2$ catalyst with a residence time of 1–12 hours.

12. A batch process according to claim 1, wherein a mixture containing phospholipase, phospholipid, fatty acid and (optionally) solvent is stirred for ½–72 hours.

13. A process according to claim 12, wherein the amount of the phospholipase catalyst is 1–10% (w/w) of the total reaction system.

14. A process according to claim 1, wherein the extracellular phospholipase $A_2$ is a venom enzyme from bee or snake venom.

15. A process according to claim 1, wherein the extracellular phospholipase $A_2$ is a digestive enzyme from a pancreas.

16. A process according to claim 1, wherein the phospholipase $A_2$ is immobilized or precipitated on a suitable carrier by precipitation or adsorption on silica or a macroporous adsorbent resin.

17. A process according to claim 1, wherein $Ca^{++}$ is present in the water phase having a $Ca^{++}$ concentration of 1 mM–1 M.

18. A process according to claim 1, wherein $Ca^{++}$ is present in the water phase as $CaCl_2$.

19. A process according to claim 1, carried out in the presence of an organic solvent selected from the group consisting of hexane, heptane, petroleum ether or a chlorinated hydrocarbon.

20. A batch process according to claim 1, wherein a mixture containing phospholipase, phospholipid, fatty acid and (optionally) solvent is stirred for 1 for ½–24 hours.

* * * * *